US006346640B1

(12) United States Patent
Slany et al.

(10) Patent No.: US 6,346,640 B1
(45) Date of Patent: Feb. 12, 2002

(54) METHOD FOR PRODUCING CYANOVALERIC ACID OR ESTERS THEREOF

(75) Inventors: Michael Slany, Kirchheim; Martin Schäfer; Michael Schulz, both of Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/763,694

(22) PCT Filed: Sep. 2, 1999

(86) PCT No.: PCT/EP99/06463

§ 371 Date: Feb. 26, 2001

§ 102(e) Date: Feb. 26, 2001

(87) PCT Pub. No.: WO00/14055

PCT Pub. Date: Mar. 16, 2000

(30) Foreign Application Priority Data

Sep. 3, 1998 (DE) .......................................... 198 40 253

(51) Int. Cl.[7] ............................................ C07L 255/00
(52) U.S. Cl. ........................................ 558/353; 558/441
(58) Field of Search ................................. 558/353, 441

(56) References Cited

U.S. PATENT DOCUMENTS

| 3,686,264 | A | 8/1972 | Albanese et al. ............ 260/465 |
| 3,869,501 | A | 3/1975 | Waddan ....................... 260/465 |
| 4,060,543 | A | 11/1977 | Weitz et al. ................. 260/464 |
| 4,257,973 | A | 3/1981 | Mrowca ....................... 260/410 |
| 4,508,660 | A | 4/1985 | Sieja .......................... 260/465 |
| 4,933,483 | A | 6/1990 | Burke et al. ................ 558/353 |

FOREIGN PATENT DOCUMENTS

| EP | 0 227 160 | 7/1987 |
| EP | 0 373 579 | 6/1990 |
| EP | 0 377 838 | 7/1990 |
| EP | 450 577 | 10/1991 |
| EP | 0 495 547 | 7/1992 |
| GB | 1104140 | 2/1968 |
| GB | 1 497 046 | 1/1978 |
| WO | WO 97/08127 | 3/1997 |

*Primary Examiner*—Joseph K. McKane
*Assistant Examiner*—Joseph Murray
(74) *Attorney, Agent, or Firm*—Keil & Weinkauf

(57) ABSTRACT

The process comprises reacting 2-, 3- or 4-pentenenitrile or mixtures thereof with carbon monoxide and a hydroxyl compound in the presence of a catalyst system comprising (i) a palladium(II) compound, (ii) a bidentate diphosphine ligand and (iii) an anion source. Novel catalyst systems containing diphosphine ligands of the bis(phosphinomethyl) amine type are also described.

7 Claims, No Drawings

METHOD FOR PRODUCING CYANOVALERIC ACID OR ESTERS THEREOF

The present invention relates to a process for preparing cyanovaleric acid or esters by reacting 2-, 3- or 4-pentenenitrile or mixtures thereof with carbon monoxide and a hydroxyl compound in the presence of a catalyst system.

5-Cyanovaleric acid and its esters are useful starting materials for dyes, pesticides, fibers, especially polyamide fibers, and plastics. Hydrogenation to 6-aminocaproic acid or 6-aminocaproic esters and elimination of water or alcohol provides caprolactam.

The preparation of cyanovaleric acid and cyanovaleric esters by carbonylation of pentenenitriles in the presence of catalysts is known. Known syntheses involve a pentenenitrile being reacted with carbon monoxide in the presence of water or alcohol at elevated temperature and elevated pressure in the presence of a catalyst system. The catalyst systems used are predominantly cobalt compounds, such as $Co_2(CO)_8$ or $Co(OAc)_2$, together with nitrogen bases (see GB-1 497 046 and DE-2 541 640), specific solvents, such as sulfolane (see U.S. Pat. No. 4,508,660), cyclic amide or urea derivatives (see EP-373 579) or nitrites (see EP-377 838 and U.S. Pat. No. 4,933,483).

EP 0 450 577 describes an Rh/HI catalyst system for hydroxycarbonylating pentenenitrile to form cyanovaleric acid.

Nitrile compounds frequently form complexes with transition metals. Catalytically active catalyst complexes tend to become deactivated through nitrile coordination. This holds especially for palladium, since palladium very readily forms stable nitrile complexes, for example $(PhCN)_2PdCl_2$, $(CH_3CN)_2PdCl_2$. The palladium-catalyzed carbonylation of olefins that contain nitrile groups therefore proceeds in general only at very low catalyst activity. For instance, U.S. Pat. No. 4,257,973 describes the carbonylation of 3-pentenenitrile using the catalyst system $(Ph_3P)_2PdCl_2/SnCl_2$. The reaction proceeds with unknown selectivity, the yield of unspecific cyanic esters being only 5% (see Example 108 of U.S. Pat. No. 4,257,973).

EP 0 495 547 describes a process for the monocarbonylation of optionally substituted olefinically unsaturated compounds in the presence of a catalyst system comprising palladium cations, a bidentate diphosphine ligand and an anion source. According to EP 0 495 547, the starting olefin can be substituted by cyano or nitrile groups, for example. When alkenoic acid derivatives, such as alkenonitriles, are used as starting materials, the alkenoic acid derivative shall preferably be a 2-alkenoic acid derivative. For the carbonylation of alkenoic acid derivatives, the catalyst system preferably comprises a promoter, for example quinones and nitro compounds. Example 59 of EP 0 495 547 carbonylates acrylonitrile with carbon monoxide and methanol in the presence of $Pd(OAc)_2$, TBPD (1,3-bis(di-n-butylphosphino) propane), NiTFS (nickel di-trifluoromethylsulfonate) and 1,4-naphthoquinone. However, conversion to the monomethyl ester mononitrile of malonic acid was only 5%, based on the acrylonitrile used. From EP 0 495 547, a person skilled in the art would have expected even lower yields for the reaction of nitrile-substituted olefins other than acrylonitrile, by the process described therein.

We have now found that, surprisingly, the carbonylation of 2-, 3- or 4-pentenenitrile is possible in high yield and high selectivity using a catalyst system which is comparable to that of EP 0 495 547. We have also found novel catalyst systems and novel diphosphine ligands whereby the yield and selectivity can be increased even further.

The present invention accordingly provides the process for preparing cyanovaleric acid or esters by reacting 2-, 3- or 4-pentenenitrile or mixtures thereof with carbon monoxide and a hydroxyl compound in the presence of a catalyst system comprising (i) a palladium(II) compound, (ii) a bidentate diphosphine ligand, and (iii) an anion source.

The starting materials used for the carbonylation of the invention are 2-, 3- or 4-pentenenitrile or mixtures thereof. The use of 3- and/or 4-pentenenitrile or of mixtures comprising 3- and/or 4-pentenenitrile as main components is preferred. 3-Pentenenitrile or mixtures comprising 3-pentenenitrile as main component are most preferred. 3-Pentenenitrile is preparable for example by addition of hydrocyanic acid to butadiene, for example in the presence of nickel complexes or copper(I) chloride according to the procedures described in the German OPI documents 1 593 277, 2 344 767 and 2 009 470.

The process of the invention provides 5-cyanovaleric acid with high selectivity, regardless of whether 2-, 3- or 4-pentenenitrile or a mixture thereof is used. It is believed that 2-pentenenitrile and 3-pentenenitrile first isomerize into 4-pentenenitrile. The carbonylation of 4-pentenenitrile to form 5-cyanovaleric acid or ester by the process of the invention takes place substantially regioselectively with selectivities which are generally above 70%, preferably above 80%, based on cyanovaleric acid or ester formed.

The palladium(II) compound is preferably a palladium salt. Examples of suitable palladium salts include the salts of nitric acid, sulfuric acid, of sulfonic acids, for example chlorosulfonic acid, methanesulfonic acid, trifluoromethanesulfonic acid, t-butylsulfonic acid, p-toluenesulfonic acid, or of a sulfonated ion exchange resin, or of a carboxylic acid, for example of an alkanoic acid, such as acetic acid or trifluoroacetic acid. It will be appreciated that when the palladium(II) compound is a palladium salt of a suitable acid, this compound may also function as the anion source to be used according to the invention. The palladium(II) compound, furthermore, may take the form of a palladium complex, for example of a complex with a bidentate diphosphine ligand. In this case, the palladium(II) compound will simultaneously contain the bidentate diphosphine ligand to be used according to the invention. The palladium(II) compound can also be formed in situ starting from the elemental state.

The amount of palladium(II) compound is not critical. The amount is preferably within the range from $10^{-7}$ to $10^{-1}$ mol of palladium per mole of pentenenitrile used, especially within the range from $10^{-6}$ to $10^{-2}$.

The bidentate diphosphine ligand can be used as such or in the form of a complex with the palladium(II) compound. Preferably, the diphosphine ligand has the following general structural formula:

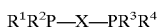

where $R^1$, $R^2$, $R^3$ and $R^4$ are independently $C_1$–$C_{20}$-alkyl, $C_3$–$C_{10}$-cycloalkyl, aryl or hetaryl having up to 4 fused aromatic rings or $C_7$–$C_{20}$-aralkyl, which may each be substituted, or $R^1$ and $R^2$ and/or $R^3$ and $R^4$ are together $C_2$–$C_{20}$-alkylene, arylene or hetarylene having up to 4 aromatic rings or $C_7$–$C_{20}$-aralkylene, which may each be substituted, and X is a divalent bridging radical such that the flanking phosphorus atoms are separated by from 1 to 10 atoms.

In more preferred diphosphine ligands, $R^1$, $R^2$, $R^3$ and $R^4$ are each independently an unsubstituted, linear or branched, linear or cyclic alkyl radical having from 1 to 10 carbon atoms, or $R^1$ and $R^2$ and/or $R^3$ and $R^4$ are together a linear or branched, linear or cyclic alkylene radical having from 1 to 10 carbon atoms.

In particularly preferred embodiments, $R^1$, $R^2$, $R^3$ and $R^4$ are each selected from methyl, ethyl, propyl, isopropyl, n-butyl, s-butyl, t-butyl and/or cyclohexyl radicals, or $R^1$ and $R^2$ and/or $R^3$ and $R^4$ are together a pentamethylene, hexamethylene or cyclooctylene radical. Where it has been stated above that $R^1$, $R^2$, $R^3$ and $R^4$ may each be substituted, the substituents can be any substituents which do not impair the catalytic activity of the system. Suitable substituents include halogen atoms, alkoxy groups, haloalkyl groups, haloalkoxy groups, acyl radicals, acyloxy groups, amino groups, hydroxyl groups, nitrile groups, acylamino groups and aryl groups.

The diphosphine ligand to be used according to the invention is bidentate; that is, it must contain the two phosphine phosphorus atoms at an intramolecular distance and in an intramolecular configuration which permit the formation of a coordinative bond on the part of both the phosphorus atoms with a single palladium atom. In the above preferred structural formula, therefore, x is a divalent bridging radical such that the flanking phosphorus atoms are separated by from 1 to 10 atoms. The bridging group preferably does not contain any substituents which could sterically hinder the coordination. Preferably, X is an alkylene chain which may contain heteroatoms, such as a divalent hydrocarbon, ether or thioether radical. Examples of bridging groups X are for example —CH$_2$—, —CH$_2$CB$_2$—, —CH$_2$CH$_2$CH$_2$—, —CH$_2$OCH$_2$—, —CH$_2$SCH$_2$—, —CH$_2$CH$_2$CH$_2$CH$_2$—, —CH$_2$CH$_2$OCH$_2$CH$_2$—, —CH$_2$CH$_2$SCH$_2$CH$_2$—, —CH$_2$CH$_2$OCH$_2$CH$_2$OCH$_2$CH$_2$—, —CH$_2$C(CH$_3$)$_2$–CH$_2$—, —CH$_2$—CH(CH$_3$)—O—CH(CH$_3$)—CH$_2$—.

Examples of suitable bidentate diphosphine ligands are accordingly: 1,2-bis(di-n-butylphosphino)ethane, 1,3-bis(dimethylphosphino)propane, 1,3-bis(diisopropylphosphino)propane, 1,3-bis(di-n-propylphosphino)propane, 1,3-bis(di-isobutylphosphino) propane, 1,3-bis(di-n-butylphosphino)propane, 1,3-bis(di-s-butylphosphino)propane, 1,3-bis(di-t-butylphosphino) propane, 1,3-bis(di-n-hexylphosphino)propane, 1,2-bis(dicyclohexylphosphino)ethane, 1,3-bis(n-butylmethylphosphino)propane, 1,3-bis(n-butylethylphosphino)propane, 1,3-bis(1,5-cyclooctylenephosphino)propane and its isomeric mixture containing 1,4-cyclooctylene groups, 1,4-bis(diisopropylphosphino)butane, 1,5-bis(dimethylphosphino)-3-oxapentane, 1,8-bis(di-n-butylphosphino)-3,6-dioxaoctane and 1,4-bis(di-n-butylphosphino)-2,2,3,3-tetramethylbutane.

In particularly preferred embodiments, X is

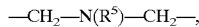
—CH$_2$—N(R$^5$)—CH$_2$—, where $R^5$ is hydrogen, straight-chain or branched $C_1$–$C_{20}$-alkyl, such as methyl, ethyl, n-propyl, isopropyl, n-butyl, s-butyl, t-butyl, pentyl, hexyl, octyl, unsubstituted or $C_1$–$C_6$-alkyl-substituted $C_3$–$C_{10}$-cycloalkyl, including bicycloalkyl, such as cyclopropyl, cyclopentyl, cyclohexyl, norbornyl, pinanyl, bornyl, bicyclononyl, unsubstituted or $C_1$–$C_6$-alkyl-substituted $C_6$–$C_{20}$-aryl, such as phenyl, tolyl, naphthyl, unsubstituted or $C_1$–$C_6$-alkyl-substituted $C_7$–$C_{20}$-aralkyl, for example having from 1 to 6 carbon atoms in the alkyl radical and from 6 to 14 carbon atoms in the aryl radical, such as benzyl, unsubstituted or $C_1$–$C_6$-alkyl-substituted $C_3$–$C_{20}$-hetaryl, such as pyridyl, pyrimidyl, pyrazinyl, triazinyl, or $C_2$–$C_{21}$-acyl.

Where the radicals mentioned can be substituted by $C_1$–$C_6$-alkyl, they can be substituted by one or more alkyl groups, for example methyl or ethyl.

The aforementioned radicals can be substituted by one or more, for example from 1 to 5, substituents selected from the group consisting of —NO, —NO$_2$, —CN, —CO$_2$, —CO$_2$R$^6$, —CONR$^6{}_2$, halogen, i.e., F, Cl, Br, I, —NR$^6{}_2$, —OR$^6$, —NR$^{6+}{}_3$, —SO$_3$—, —SO$_3$R$^6$, —SO$_2$R$^6$, SO$_2$NR$^6{}_2$ and SiR$^7{}_3$, where $R^6$ is hydrogen, $C_1$–$C_{10}$-alkyl, especially methyl, ethyl or isopropyl, or $C_6$–$C_{14}$-aryl, especially phenyl, and $R^7$ is $C_1$–$C_{10}$-alkyl, especially methyl, ethyl or isopropyl, or $C_6$–$C_{14}$-aryl, especially phenyl. Moreover, in the aforementioned radicals, 1, 2, 3 or 4 carbon atoms can be replaced by N or O.

$R^5$ can be for example the group —(CH$_2$)$_n$–Q, which may be substituted and may contain heteroatoms, such as oxygen or nitrogen, or arylene units, such as phenylene, in the alkylene chain, in which case Q is —SO$_3$—, CO$_2$—CO$_2$R$^6$, —CONR$^6{}_2$, halogen, —NR$^6{}_2$, —OR$^6$, NR$^{6+}{}_3$ and n=1–20, particularly preferably 1–10. $R^5$ can also be SiR$^7{}_3$, such as trimethylsilyl, t-butyldimethylsilyl, triphenylsilyl.

It is preferred that $R^5$ is an electron-attracting radical, since this increases the stability of the diphosphine compound. Suitable electron-attracting radicals $R^5$ are linear or branched $C_1$–$C_{20}$-alkyl substituted by at least one electron-attracting group, the electron-attracting group being preferably disposed in the α-, β-, γ- and/or δ-position, especially in the α- and/or β-position relative to the nitrogen atom, $C_6$–$C_{14}$-aryl which is substituted by at least one electron-attracting group, and also nitrile, sulfinyl (—SO$_2$R$^7$), sulfonyl (—SO$_3$R$^7$) and nitro groups. $R^5$ may also be —C(O)R$^8$, in which case $R^8$ is linear or branched $C_1$–$C_{20}$-alkyl, $C_6$–$C_{14}$-aryl or aralkyl having from 1 to 10 carbon atoms in the alkyl moiety and from 6 to 14 carbon atoms in the aryl moiety, linear or branched $C_1$–$C_{20}$-alkyl substituted by at least one electron-attracting group, the electron-attracting group being preferably disposed in the α-, β-, γ- and/or δ-position relative to the C(O) group, and also $C_6$–$C_{14}$-aryl which is substituted by at least one electron-attracting group. Preferred $R^8$ radicals include methyl, ethyl, isopropyl, phenyl, trifluoromethylphenyl, trifluoromethyl or pentafluoroethyl.

Suitable electron-attracting substituents on an alkyl or aryl $R^5$ are halogen atoms, such as fluorine, chlorine or bromine, preferably fluorine and chlorine, particularly preferably fluorine. The alkyl and aryl radicals may be both partially halogenated and perhalogenated. Furthermore, the nitro, nitrile, ester, amide, sulfinyl, sulfonylamide and sulfonyl group is useful as a substituent for the alkyl and aryl radicals. The aryl radicals may also be substituted by trifluoro- or trichloromethyl groups and also by ammonium radicals. Examples of suitable alkyl radicals $R^5$ are: trifluoromethyl, trichloromethyl, difluoromethyl, 2,2,2-trifluoroethyl, 2,2,2-trichloroethyl, 3,3,3-trifluoropropyl, pentafluoroethyl, nitromethyl, 2-nitromethyl, 2-nitroethyl and cyanomethyl. Preference is given to trifluoromethyl and 2,2,2-trifluoroethyl. Examples of suitable aryl radicals $R^5$ are p-, m-, o-fluoro- or chlorophenyl, 2,4-difluorophenyl, 2,4-dichlorophenyl, 2,4,6-trifluorophenyl, pentafluorophenyl, 2,4,6-trichlorophenyl, nitrophenyl, 2,4-dinitrophenyl, 2-chloro-5-nitrophenyl, 2-bromo-5-nitrophenyl, methylsulfinylphenyl and methylsulfonylphenyl.

The invention also provides a catalyst composition comprising a palladium(II) compound and a diphosphine compound of the general structural formula R$^1$R$^2$P—CH$_2$—N(R$^5$)—CH$_2$—PR$^3$R$^4$, where $R^1$ to $R^5$ have the abovementioned meanings and preferred meanings. In particularly preferred embodiments of the catalyst composition of the invention, $R^1$ and $R^2$ on the one hand and $R^3$ and $R^4$ on the other are jointly and independently 1,3- and/or 1,4-cyclooctylene and $R^5$ is 2,4-difluorophenyl, pentafluorophenyl or 2,4,6-trifluorophenyl.

As regards the palladium(II) compound, reference is made to the observations made at the outset. The catalyst composition may include an anion source or be used with an anion source. When the palladium(II) compound is the palladium salt of a suitable acid, this acid may at the same time function as the anion source.

Such diphosphine compounds are also referred to as bis(phosphinomethyl)amines. The preparation of some representatives has been described by J. Fawcett, P.A.T. Hoye et al. in J. Chem. Soc. Dalton Trans. 1993, 2563–2567.

Some of the bis(phosphinomethyl)amines are new. The invention accordingly also provides diphosphine compounds of the general structural formula

where $R^1$ to $R^5$ possess the abovementioned meanings and preferred meanings, with the proviso that compounds where $R^1$, $R^2$, $R^3$ and $R^4$ are each phenyl and $R^5$ is CHMePh, CHMeCO$_2$Me, CHMeCO$_2$Et, endo-(1R)-1,7,7-trimethylbicyclo[2.2.1]heptan-2-yl, CH$_2$CH$_2$OH or CH$_2$CH=CH$_2$; $R^1$, $R^2$, $R^3$ and $R^4$ are each cyclohexyl and $R^5$ is CHMePh or CHMeCO$_2$H; or $R^1$ and $R^2$ on the one hand and $R^3$ and $R^4$ on the other are together cyclooctylene and $R^5$ is CHMePh shall be excluded. (Me is methyl, Et is ethyl and Ph is phenyl.)

The preparation of the bis(phosphinomethyl)amines is accomplished for example according to the following general reaction scheme:

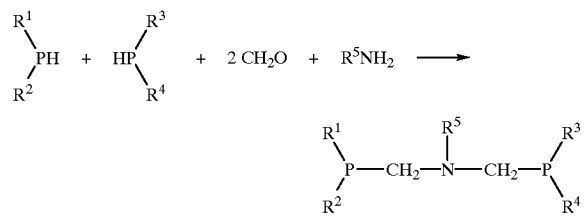

The reaction conditions may conveniently be chosen to be similar to those described in J. Fawcett, P.A.T. Hoye, et al., J. Chem. Soc. Dalton Trans. 1993, 2563–2567. Thus, the bis(phosphinomethyl)amines are readily preparable in a one-pot reaction by reacting the secondary phosphine with formaldehyde and ammonia or a primary amine, for example in a solvent, such as toluene, at a temperature of from preferably 80° C. to 150° C.

The molar ratio of diphosphine compound to palladium (II) compound, based on palladium, is preferably within the range from 0.5 to 20:1, especially within the range from 1 to 5:1.

Useful anion sources include Lewis and protic acids and mixtures thereof. The anion sources used are preferably weak organic acids, for example organic acids having a pK$_a$ value of 3.5 or higher, especially sterically hindered organic acids. Examples of preferred organic acids are benzoic acid, 2,4,6-trimethylbenzoic acid, 2,6-dichlorobenzoic acid, 9-anthracenecarboxylic acid, pivalic acid, 1,2,3-benzenetricarboxylic acid and its partial esters, 2-ethoxy-l-naphthalenecarboxylic acid, 2,6-dimethoxybenzoic acid, acetic acid, propionic acid, butyric acid and/or cyanovaleric acid.

It is also possible to use strong mineral acids, such as sulfuric acid, perchloric acids and also strong organic acids, such as sulfonic acids, e.g., methanesulfonic acid, p-toluenesulfonic acid and benzenesulfonic acids and also trichloro- and trifluoroacetic acid.

The molar ratio of anion source to palladium(II) compound is not critical. The molar ratio of anion source to palladium(II) compound is preferably within the range of 0.5–100:1, especially within the range of 1–10:1, equivalents per mole of palladium.

The use of cyanovaleric acid is particularly preferable, since in this case the by-produced ester of the organic acid anion source with the hydroxyl compound for example an alcohol, does not lead to a contamination of the reaction product obtained.

The hydroxyl compound used in the process of the invention can be for example water or an alcohol, especially an alcohol having 1–6 carbon atoms. The alcohol used can be any primary, secondary or tertiary alcohol. Examples of preferred alcohols include methanol, ethanol, propanol, isopropanol, butanols, n-hexanol, n-octanol, isooctanol, 2-ethylhexanol, cyclohexanol, benzyl alcohol, phenylethyl alcohol, ethylene glycol, 1,2-propylene glycol, 1,3-propylene glycol, neopentylglycol, trimethylolpropane and pentaerythritol. Particular preference is given to methanol and ethanol.

The process of the invention is advantageously carried out at 40–200° C., preferably 75–170° C. The process of the invention may advantageously be carried out at a pressure of 1–200 bar, preferably 5–70 bar. The reaction may be carried out under batchwise, continuous or semicontinuous conditions. The reaction times are generally within the range from 0.5 hours to 10 hours.

The catalyst system to be used according to the invention may be homogeneous or heterogeneous. The catalyst system may also be used in immobilized form. Examples of suitable supports are ion exchangers, in which case, for example, ionic groups on the diphosphine compound, for example certain above-defined substituents Q in $R^5$, enter into interaction with ionic groups on the ion exchanger. Immobilization may be effected by adding a solution of the catalyst system to the ion exchanger and the catalyst system becoming fixed.

The process of the invention is preferably carried out in the liquid phase. The liquid phase may be formed by the pentenenitrile used or by the hydroxyl compound used. Alternatively or additionally, the liquid phase may also comprise a solvent. Any inert solvent may be used. Examples are sulfoxides and sulfones, e.g., dimethyl sulfoxide, diisopropyl sulfone or tetrahydrothiophene 2,2-dioxide, 2-methylsulfolane, 3-methylsulfolane, 2-methyl-4-butylsulfolane; aromatic hydrocarbons, such as benzene, toluene, xylene; esters, such as methyl acetate and butyrolactone; ketones, such as acetone or methyl isobutyl ketone; alcohols, such as methanol and ethanol, ethers, such as tetrahydrofuran, anisole, 2,5,8-trioxanonane, diphenyl ether and diisopropyl ether; amides, such as dimethylacetamide and N-methylpyrrolidone.

The process of the invention preferably takes place in the substantial absence of oxygen. For this purpose, the reaction vessel is, for example, repeatedly evacuated and filled with a protective gas, for example nitrogen. Reactants, solvent and catalyst system are added in the absence of a ir.

The process of the invention may be carried out for example as follows: 2-Pentenenitrile, 3-pentenenitrile, 4-pentenenitrile or a mixture thereof, the hydroxyl compound, the catalyst system and, as the case may be, a solvent are introduced into a pressure-resistant reactor. This is followed by injection of carbon monoxide and the heating of the reactor to the desired reaction temperature. The reaction pressure may be adjusted, if necessary, by injecting further carbon monoxide or by releasing carbon monoxide. After the reaction has ended, the mixture may be cooled down and decompressed. The cyanovaleric acid or its esters may be isolated from the mixtures by customary methods, for example by fractional distillation.

The catalyst system used may be formed in situ under the reaction conditions. Alternatively and preferably, however, the catalyst system is prepared in advance. To this end, for example, the palladium(II) compound, the bidentate diphosphine ligand and, if necessary, an anion source are each dissolved or suspended in mutually miscible solvents and the solutions or suspensions combined. The palladium(II) diphosphine complex may then be isolated, for example by filtration, if necessary after addition of a solubility-reducing diluent.

The Examples which follow illustrate the invention.

EXAMPLE 1

28 mg (0.125 mmol) of palladium(II) acetate, 155 mg (0.5 mmol) of a mixture of 1,3-bis(1,5-cyclooctylenephosphino) ethane and 1,2-bis(1,4-cyclooctylenephosphino)ethane and of the mixed compounds with 1,5- and 1,4-cyclooctylene groups (bcope), 445 mg (2.0 mmol) of 9-anthracenecarboxylic acid and 3 ml (31 mmol) of 3-pentenenitrile were taken up in 10 ml of diphenyl ether and 5 ml of methanol and introduced into a 100 ml autoclave. The autoclave was sealed and carbon monoxide was injected to a pressure of 40 bar. The autoclave was heated to 150° C. and the total pressure was adjusted to 60 bar. Following the reaction time reported in Table 1, the reaction was terminated by cooling the autoclave. The autoclave was decompressed and the liquid effluent was analyzed by gas chromatography.

EXAMPLE 2

Example 1 was repeated in a 300 ml autoclave using the following reactants in the stated amounts: 112 mg (0.5 mmol) of palladium(II) acetate, 845 mg (2.0 mmol) of 1,2-bis(dicyclohexylphosphino)ethane, 2.2 g (10 mmol) of 9- anthracenecarboxylic acid, 12 ml (124 mmol) of 3-pentenenitrile, 20 ml of methanol and 40 ml of diphenyl ether.

EXAMPLE 3

Example 1 was repeated using the following reactants in the stated amounts: 28 mg (0.125 mmol) of palladium(II) acetate, 116 mg (0.375 mmol) of bcope, 445 mg (2.0 mmol) of 9-anthracenecarboxylic acid, 10 ml (103 mmol) of 3-pentenenitrile and 15 ml of methanol.

EXAMPLE 4

The palladium(II) diphosphine complex was prepared in advance for this Example.

1.0 g (4.4 mmol) of palladium(II) acetate was dissolved in 50 ml of acetone, and the solution was stirred for 2 hours at room temperature and filtered through celite. The filtrate was admixed with a suspension of 2.1 g (4.4 mmol) of bcope in 50 ml of acetone and stirred at room temperature for 1 h. The resulting pale yellow solid (bcope)Pd(OAc)$_2$ was filtered off and dried under reduced pressure. Yield: 2.2 g (94%).

Example 1 was repeated using the following reactants in the stated amounts: 67 mg (0.125 mmol) of (bcope)Pd(OAc)$_2$, 445 mg (2.0 mmol) of anthracenecarboxylic acid, 10 ml (103 mmol) of 3-pentenenitrile and 15 ml of methanol. The results are in each case reported in the following table:

| Example | Reaction time | Conversion of 3-PN | TON | TOF | Sel. (CVE) | Sel. (5-CVE) |
|---|---|---|---|---|---|---|
| 1 | 6 h | 90% | 192 | 32 | 90% | 70% |
| 2 | 15 h | 40% | 85 | 14 | 90% | 71% |
| 3 | 3 h | 57% | 470 | 157 | 90% | 72% |
| 4 | 3 h | 62% | 494 | 165 | 90% | 72% |

CVE = cyanovaleric ester
TON = turn over number
TOF = turn over frequency

Comparing Example 4 with Example 3 shows that using the preprepared, defined (bcope)Pd(OAc)$_2$ complex improves the catalyst activity. A further advantage with the use of the defined, preprepared complex is that there is no need for an excess of diphosphine compound.

EXAMPLE 5

This Example illustrates the preparation of a mixture of 1,3-bis (1,4-cyclooctylenephosphinomethyl)phenylamine, 1,3-bis(1,5-cyclooctylenephosphinomethyl)phenylamine, 1-(1,4-cyclooctylenephosphinomethyl)-3-(1,5-cyclooctylenephosphinomethyl)phenylamine.

1.2 g (0.035 mol) of paraformaldehyde are suspended in 100 ml of toluene and the suspension is heated to 65 ° C. 1.6 ml (0.0175 mol) of aniline and 5 g (0.035 mol) of a mixture of 1,4-cyclooctenylphosphine and 1,5-cyclooctenylphosphine are added. A clear solution is obtained after 5 h, cooled down and concentrated. The residue is taken up in 50 ml of dichloromethane and the chelate phosphine is precipitated with ethanol. After filtration, the white residue is dried under reduced pressure. Yield: 4.8 g (68%).

EXAMPLE 6

This Example illustrates the preparation of 1,3-bis(1,4-cyclooctylenephosphinomethyl)(2,4-difluorophenyl)amine, 1,3-bis(1,5-cyclooctylenephosphinomethyl)(2,4-difluorophenyl)amine, 1-(1,4-cyclooctylenephosphinomethyl)-3-(1,5-cyclooctylenphosphinomethyl)(2,4-difluorophenyl)amine (aza-bcope).

1.2 g (0.035 mol) of paraformaldehyde are suspended in 100 ml of toluene and the suspension is heated to 65° C. 1.8 ml (0.0175 mol) of 2,4-difluoroaniline and 5 g (0.035 mol) of a mixture of 1,4-cyclooctenylphosphine and 1,5-cyclooctenylphosphine are added and the solution is stirred overnight at 65° C. After cooling the solvent is drawn off under reduced pressure, the residue is taken up in 20 ml of dichloromethane and the product is precipitated with ether. The white solid is filtered and dried under reduced pressure. Yield: 5.4 g (70%).

EXAMPLE 7

This Example illustrates the preparation of a mixture of the complexes 1,3-bis(1,4-cyclooctylenephosphinomethyl) (2,4-difluorophenyl)amine-Pd(OAc)$_2$, 1,3-bis(1,5-cyclooctylenephosphinomethyl)(2,4-difluorophenyl)amine-Pd(OAc)$_2$ and 1-(1,4-cyclooctylenephosphinomethyl)-3-(1, 5-cyclooctylenephosphinomethyl)(2,4-difluorophenyl) amine-Pd(OAc)$_2$.

0.45 g (2.0 mmol) of palladium(II) acetate was dissolved in 50 ml of acetone, stirred at room temperature for 2 h and filtered through Celite. The filtrate was admixed with a suspension of 0.88 g (2.2 mmol) of aza-bcope in 50 ml of acetone and stirred at room temperature for 1 h. The resulting pale yellow solid was filtered off and dried under reduced pressure. Yield: 1.1 g (88%).

EXAMPLE 8

This Example illustrates the carbonylation of 3-pentenenitrile using the (aza-bcope)Pd(OAc)$_2$ complex. Example 1 was repeated using the following reactants in the stated amounts: 79 mg (0.125 mmol) of (aza-bcope)Pd (OAc)$_2$ (see Example 7), 445 mg (2.0 mmol) of anthracenecarboxylic acid, 10 ml (103 mmol) of 3-pentenenitrile and 15 ml of methanol.

| Example | Reaction time | Conversion of 3-PN | TON | TOF | Sel. (CVE) | Sel. (5-CVE) |
|---|---|---|---|---|---|---|
| 8 | 3 h | 75% | 598 | 200 | 90% | 71% |

Comparing Example 8 with Example 4 shows that the catalyst system (aza-bcope)Pd(OAc)$_2$ has distinctly higher catalyst activity.

We claim:

1. The process for preparing cyanovaleric acid or esters by reacting 2-, 3- or 4-pentenenitrile or mixtures thereof with carbon monoxide and a hydroxyl compound in the presence of a catalyst system comprising:
   (i) a palladium(II) compound
   (ii) a bidentate diphosphine ligand, and
   (iii) an anion source.

2. The process of claim 1, wherein the diphosphine ligand has the following general structural formula:

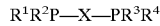

where $R^1$, $R^2$, $R^3$ and $R^4$ are independently $C_1$–$C_{20}$-alkyl, $C_3$–$C_{10}$-cycloalkyl, aryl or hetaryl having up to 4 fused aromatic rings, $C_7$–$C_{20}$-aralkyl, which may each be substituted, or $R^1$ and $R^2$ and/or $R^3$ and $R^4$ are together $C_2$–$C_{20}$-alkylene, arylene or hetarylene having up to 4 aromatic rings or $C_7$–$C_{20}$-aralkylene, which may each be substituted, and X is a divalent bridging radical such that the flanking phosphorus atoms are separated by from 1 to 10 atoms.

3. The process of claim 2, wherein $R^1$, $R^2$, $R^3$ and $R^4$ are each independently an unsubstituted, linear or branched, linear or cyclic alkyl radical having from 1 to 10 carbon atoms, or $R^1$ and $R^2$ and/or $R^3$ and $R^4$ are together a linear or branched, linear or cyclic alkylene radical having from 1 to 10 carbon atoms.

4. The process of claim 3, wherein $R^1$, $R^2$, $R^3$ and $R^4$ are each selected from methyl, ethyl, propyl, isopropyl, n-butyl, s-butyl, t-butyl and/or cyclohexyl radicals, or $R^1$ and $R^2$ and/or $R^3$ and $R^4$ are together a pentamethylene, hexamethylene or cyclooctylene radical.

5. The process of claim 2, wherein X is an alkylene chain which may contain heteroatoms.

6. The process of claim 5, wherein X is

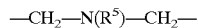

where $R^5$ is hydrogen, $C_1$–$C_{20}$-alkyl, unsubstituted or $C_1$–$C_6$-alkyl-substituted $C_3$–$C_{10}$-cycloalkyl, unsubstituted or $C_1$–$C_6$-alkyl-substituted $C_6$–$C_{20}$-aryl, unsubstituted or $C_1$–$C_6$-alkyl-substituted $C_7$–$C_{20}$-aralkyl, unsubstituted or $C_1$–$C_6$-alkyl-substituted $C_3$–$C_{20}$-hetaryl, $C_2$–$C_{21}$-acyl, the aforementioned radicals may be substituted by substituents selected from the group consisting of —NO, —NO$_2$, —CN, —CO$_2$—, —CO$_2$R$^6$, —CONR$^6$$_2$, halogen, —NR$^6$$_2$, —OR$^6$, —NR$^6$$_3$+, —SO$_3$$^-$, —SO$_3$R$^6$, —SO$_2$R$^6$, SO$_2$NR$^6$$_2$ and SiR$^7$$_3$, and/or 1, 2, 3 or 4 carbon atoms in the aforementioned radicals may be replaced by N or O, or $R^5$ is nitro, nitrile, sulfinyl, sulfonyl or SiR$^7$$_3$, $R^6$ is hydrogen, $C_1$–$C_{10}$-alkyl or $C_6$–$C_{14}$-aryl and $R^7$ is $C_1$–$C_{10}$-alkyl or $C_6$–$C_{14}$-aryl.

7. The proces of claim 2, wherein the anion source is an organic acid having a pK$_a$ value of 3.5 or higher.

* * * * *